(12) United States Patent
Gilberti (10) Patent No.: US 6,191,428 B1
(45) Date of Patent: Feb. 20, 2001

(54) ULTRAVIOLET SHUTTER

(75) Inventor: Joseph J. Gilberti, 45 Long View Rd., Avon, CT (US) 06001

(73) Assignee: Joseph J. Gilberti, Avon, CT (US)

( * ) Notice: Under 35 U.S.C. 154(b), the term of this patent shall be extended for 0 days.

(21) Appl. No.: 09/109,294

(22) Filed: Jun. 30, 1998

(51) Int. Cl.$^7$ ..................................................... A61L 2/10
(52) U.S. Cl. .......................... 250/504 R; 250/503.1; 250/493.1; 250/498.1; 378/160
(58) Field of Search ............................ 250/504 R, 503.1, 250/493.1, 498.1; 359/232, 233, 234; 378/160

(56) References Cited

U.S. PATENT DOCUMENTS 3,819,929 * 6/1974 Newman ........................... 240/41.37
5,788,940 * 8/1998 Cicha et al. ........................... 422/24
5,861,633 * 1/1999 Mandellos ........................ 250/504 R

* cited by examiner

Primary Examiner—Bruce C. Anderson
Assistant Examiner—Nikita Wells
(74) Attorney, Agent, or Firm—Alix, Yale & Ristas, LLP (57) ABSTRACT

An arrangement of shutter segments each having longitudinally opposed ends, front and back edges, and top and bottom solid surfaces, wherein each segment is adjacent to at least one other segment. The segments are arranged with the front and back edges of each segment in parallel along a first direction, and with one of the front or back edge of each segment overlapping one of the top or bottom surfaces of an adjacent segment. A drive hub is rigidly connected to each segment, respectively. A drive train engages all of the drive hubs, for simultaneously reciprocating the hubs and connected shutter segments rotatively through an actuation angle of no more than approximately 90 degrees (preferably 45 degrees) around respective axes of rotation which are parallel and coplanar along the first direction. This is especially effective when the source of UV light is arranged according to another aspect of the present invention, in which an elongated parabolic reflector surrounds an elongated UV source tube, which are situated above and substantially perpendicularly relative to, the longitudinal orientation of the shutters.

26 Claims, 6 Drawing Sheets

ULTRAVIOLET SHUTTER

BACKGROUND OF THE INVENTION

The present invention relates to apparatus and method for exposing curable material to high intensity ultraviolet light.

Of particular relevance to the present invention, are systems and methods by which curable material forms part of a protective or decorative surface on objects that, typically are of a size which can be held in a human hand, and which are to be processed at a relatively high rate. This processing can be of a high speed batch type, whereby each object having curable material thereon, is fixtured in spaced relation from a series of other such objects, and conveyed to a particular location where each object is subjected to high intensity ultraviolet (UV) curing light. The light passes through a shutter which opens and closes to control the duration of the curing exposure. Such conveying can be implemented by an indexing conveyor, such as a rotary indexing table of the type described in pending U.S. patent application Ser. No. 08/668,445 filed Jun. 20, 1996 for "Rotary Indexing Table", now U.S. Pat. No. 5,784,932 the disclosure of which is hereby incorporated by reference.

Indexing conveyors have been used in the decorating field for screen printing, hot stamping, pad printing, ink-jet printing, impact marking, laser marking, spray painting and other decorative purposes. As one particular example, rotary indexing tables are employed for multi-color screen printing onto work pieces such as compact discs, credit cards, key fobs etc. Typically, the dial of a rotary indexing table supports multiple, equidistantly positioned fixtures. The fixtures support the work pieces during the printing and curing operations. At a first work station (or section of a work station), a work piece is automatically positioned onto the fixture. The dial then rotates through a precise angle or distance to position the work piece under a first screen printing apparatus. The dial is thereafter indexed one more increment such that the work piece is positioned beneath a source of UV light. A shutter is opened, the work piece is exposed for a preset time interval during the dwell time of the indexing conveyor, and the shutter is then closed. The dial is then indexed for the screen printing of a subsequent pattern or image, and indexed again for another UV curing step, whereby the process continues until all the printing and curing has been completed for a particular work piece.

In the particular example of the work piece being a compact disc, the work piece is generally flat, with a length and width that are measured in inches, e.g., a compact disc is typically about 5 inches in diameter.

In conventional equipment of the type employed for such UV curing, the shutter system may have single or dual slide gates, single or dual pivoting reflectors, or so-called "bombay doors". For example, if two bombay doors open and close across a six by six area, each door is rotated 90° downward to a substantially vertical orientation, for opening the shutter. Of course, the doors would then each rotate 90° back to the horizontal, for closing the shutters. Therefore, the exposure of the work piece below the shutter would have a duration determined in part by the time required for the doors to cycle 180°, i.e., actuate 90° to full open, then actuate 90° to full closure.

One can readily appreciate that with an indexing conveyor system, whereby a series of work pieces are conveyed beneath the shutter, so that an individual work piece periodically is located in a stationary condition for a predetermined time interval, the center of the work piece (which lies directly under the juncture of the bombay or other conventional doors), will receive significantly more UV exposure than the outer surfaces of the work piece. This can present a problem because curing of UV inks or adhesives, requires a precise and even dosage of light energy for optimum results. Moreover, not only do the bombay doors and other conventional types of shutters produce uneven exposure, but the speed at which the shutters can operate through a full cycle, is limited by the need to mechanically accelerate and decelerate one or two relatively larger shutter elements through 180° of angular motion (i.e., 90° clockwise to open and then 90° counter-clockwise to close), or through a complete reversal of linear sliding.

SUMMARY OF THE INVENTION

It is, accordingly, an object of the present invention to provide a system and method for reducing the cycle time and improving the exposure control of a UV shutter assembly of the type used in curing work pieces.

It is a particular object to provide a system and method for reducing the cycle time and improving the exposure control of a UV shutter assembly of the type used in curing work pieces on an indexing conveyor or the like, where the work piece is stationary during UV exposure.

It is a more particular object of the invention, to provide a system and method for periodically positioning curable material at a location subject to high intensity UV curing light passing through a shutter assembly which opens and closes at a faster than conventional speed to better control the duration of curing exposure.

It is still a further object of the invention to provide a system and method for exposing curable material to high intensity UV light through a shutter assembly for a target exposure interval, wherein the actuation time for the shutters to open plus the actuation time for the shutters to close (i.e., the cycle time) totals less than ten percent of the target exposure interval, whereby work pieces carrying UV curable material are subjected to exposure that is more uniform over the surface of the work piece, than is available conventionally.

According to a broad aspect of the invention, the UV shutter assembly comprises at least three shutter segments, which can be simultaneously actuated through an included angle of no greater than about 90°.

Preferably, at least four shutter segments are provided, with each segment in the closed configuration, forming an acute angle relative to, and overlapping with, an adjacent segment.

It is a further preferred feature that the simultaneously actuated shutter segments be driven through an included angle of about 45° for each segment to open, and about 45° for each segment to close, for a total of about 90° rotation during a full cycle of operation.

The invention is preferably implemented in an arrangement of at least four shutter segments each having longitudinally opposed ends, front and back edges, and top and bottom solid surfaces, wherein each segment is adjacent at least one other segment. The segments are arranged with the front and back edges of each segment in parallel along a first direction, and with one of the front or back edge of each segment substantially abutting and preferably overlapping one of the top or bottom surfaces of an adjacent segment. A drive hub is rigidly connected to each segment, respectively. A drive train engages all of the drive hubs, for simultaneously reciprocating the hubs and connected shutter segments rotatively through an actuation angle of no more than approximately 90° around respective axes of rotation which are parallel and coplanar along the first direction.

In one embodiment, a pinion gear is operatively connected respectively to each drive hub. Each pinion gear engages an adjacent pinion gear. One of the gears is driven, whereby all gears rotate to open and close the shutter assembly.

In a second embodiment, the drive train includes a plurality of pinion gears operatively connected respectively to each drive hub, but not directly to each other. A first drive rack operatively engages a first set of pinion gears consisting of every other one of the pinion gears. A second drive rack operatively engages a second set of pinion gears consisting of all the pinion gears that are not engaged by the first drive rack. The first and second drive racks are reciprocated synchronously and in opposite directions, whereby the first set of pinion gears all reciprocate clockwise then counterclockwise in unison, while the second set of pinion gears all rotate counterclockwise then clockwise in unison.

It should thus be appreciated that even with the simplest embodiment of the invention, where at least three, and preferably up to ten shutter segments are oriented in a substantially planar fashion to close the exposure opening, and are each rotated 90° to the full open position and then returned 90° to the closed position, significant speed of operation can be achieved relative to conventional systems. For example, with a six inch wide opening, each door of a bombay arrangement would have a length of about six inches, and a width of about three inches, whereas with the present invention implemented using six segments, each segment is six inches long and only one inch wide. The energy required for rotating a shutter of given composition, having a one inch "radius" versus a three inch "radius", is higher by a factor greater than three. Moreover, the kinetic energy of the larger shutter is greater by a factor of more than three relative to the one inch radius shutter, and therefore backlash, wear, maintenance of tolerances, and similar considerations are much easier to control for the smaller shutter segment. This all contributes to significant capability for increased actuation speed.

Furthermore, a shutter arrangement having more than two segments, improves the distribution of localized exposure on the work piece. Whereas in the case of e.g., bombay doors, the center of the work piece has the highest exposure and the exposure drops continuously toward the edges away from the center, in an arrangement having six, or preferably ten segments, at least two, and preferably five regions of respectively higher and lower exposure are produced which, although not exactly uniform over the entire work piece, nevertheless produces a spatially averaging effect which is an improvement over the conventional exposure distribution.

This is especially effective when the source of UV light is arranged according to another aspect of the present invention, in which an elongated parabolic reflector surrounds an elongated UV source tube, which are situated above and substantially perpendicularly relative to, the longitudinal orientation of the shutters.

The foregoing advantages of increased speed and improved spatial distribution of the exposure on the work piece, are achieved with even greater effect in the preferred embodiment wherein the adjacent segments of the closed configuration are at an acute angle to each other, and wherein the included angle for each of the opening and closing movements, is significantly less than 90°, preferably about 45°. In a mechanically linked system, this travel of 45° permits the use of a rotary actuator which delivers a mechanically "harmonic" acceleration and deceleration, over relatively short travel distances. This provides smooth, high speed motion without excessive shock or noise.

In a typical screen printing process for which the present application finds especially good use, the optimum cure time for the ink is one second of exposure at the nominal UV intensity. However, as identified above, in order for the outer portions of the work piece to receive the desired exposure, the center of the work piece may very well receive twice as much exposure. Whereas in practice, a bombay door type shutter arrangement would typically take one half second to open and one half second to close, the preferred embodiment of the present invention can take less than 0.1 second to open, and 0.1 second to close. Although the required exposure is typically greater than 0.2 seconds, this significantly greater actuation speed permits a significant improvement in uniformity of exposure.

BRIEF DESCRIPTION OF THE DRAWINGS

FIG. 4 is a view of the shutter arrangement of the present invention;

taken along line 4 of FIG. 3;

DESCRIPTION OF THE PREFERRED EMBODIMENT

Figure 1:
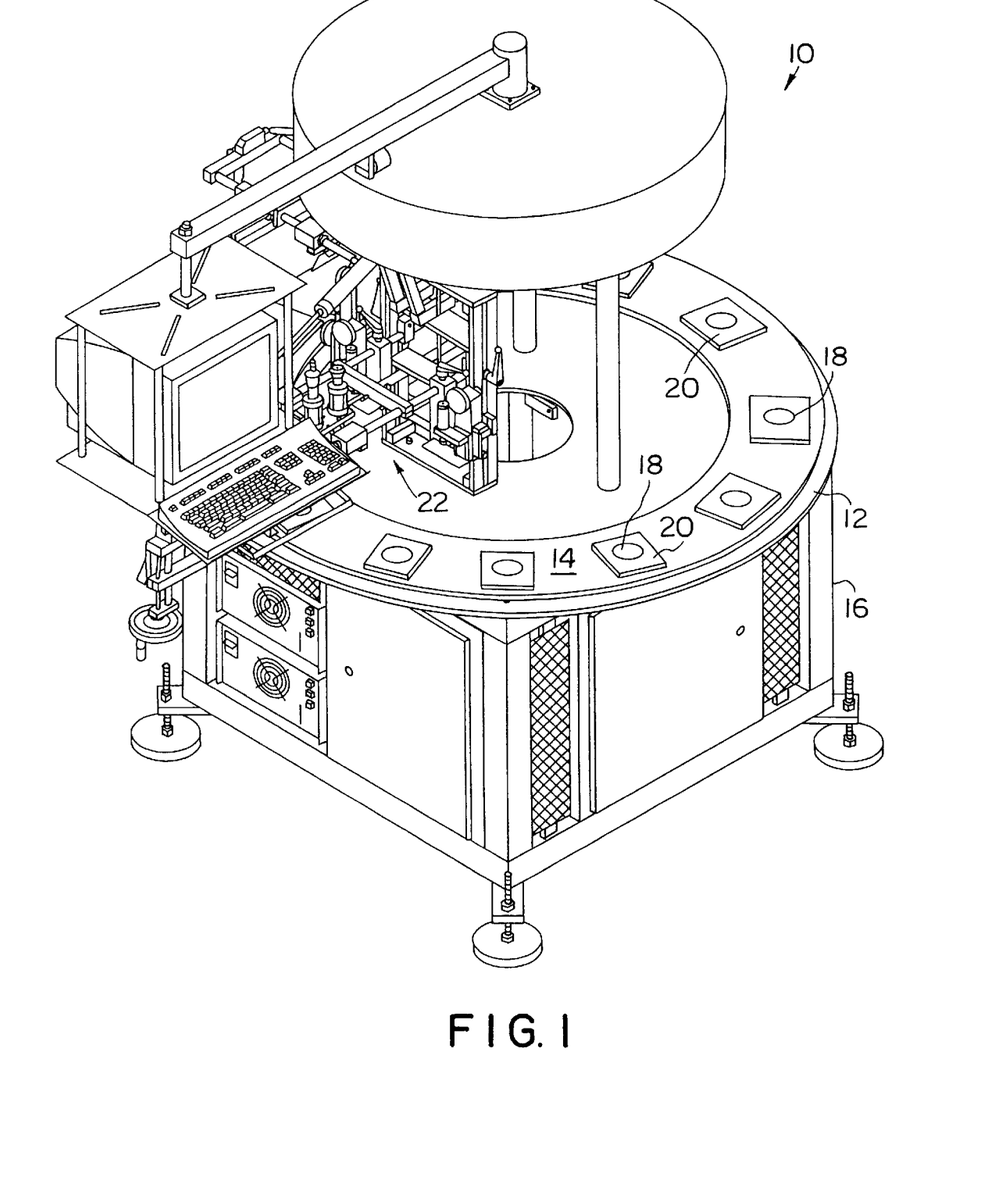
FIG. 1 represents a rotary indexing table with a work station which can include a high intensity UV curing station having a shutter arrangement according to the present invention.
Figure 2:
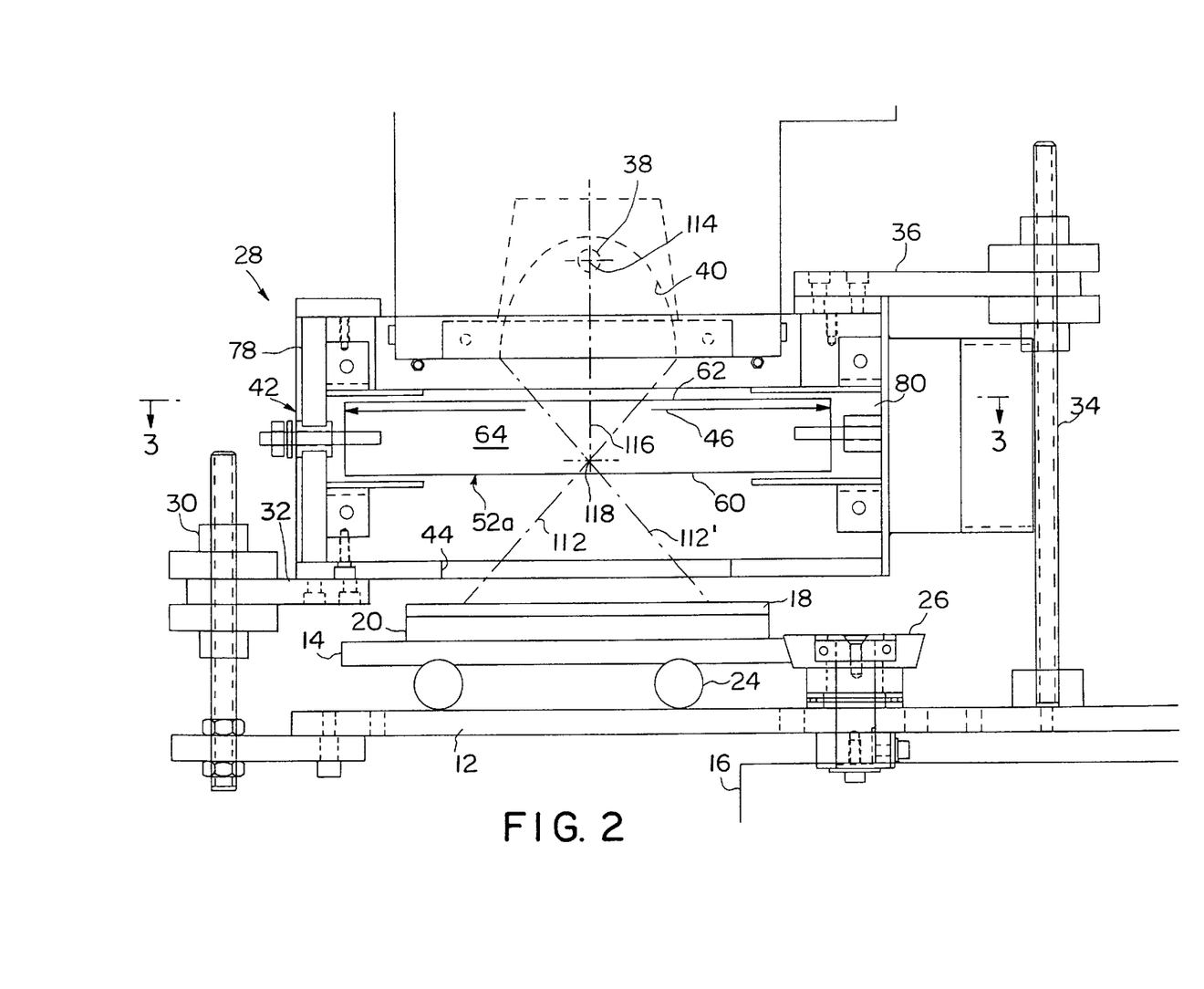
FIG. 2 is a schematic view of a UV curing station incorporating the present invention, as can be implemented in the rotary indexing table of FIG. 1.

As shown in FIGS. 1 and 2, a rotary indexing table of the type in which the present invention may be utilized, is generally designated by the numeral 10. In general, the indexing table includes a stationary base 16, a stationary platform 12 and a rotatable annulus or dial 14 which is controlled for indexed motion, such that work pieces, in this case compact discs 18 carried on respective pallets 20, are sequentially indexed into a work station 22, maintained at a pre-established location for a pre-established time interval, and then indexed to a subsequent location. The particular operational details of the indexing table shown in FIG. 1 are not relevant to the invention, and it should be appreciated that a linear or other conveying system is likewise suitable for use with the present invention.

For purposes of the present invention, it can be assumed that the rotating dial 14 is supported by ball bearings 24 on the stationary platform 12, and the dial is rotated into and out of the plane of the paper of FIG. 2 via means (not shown) engaging the outer circumference of the dial, while the inner circumference is supported internally by a fixed bearing 26.

Figure 3:
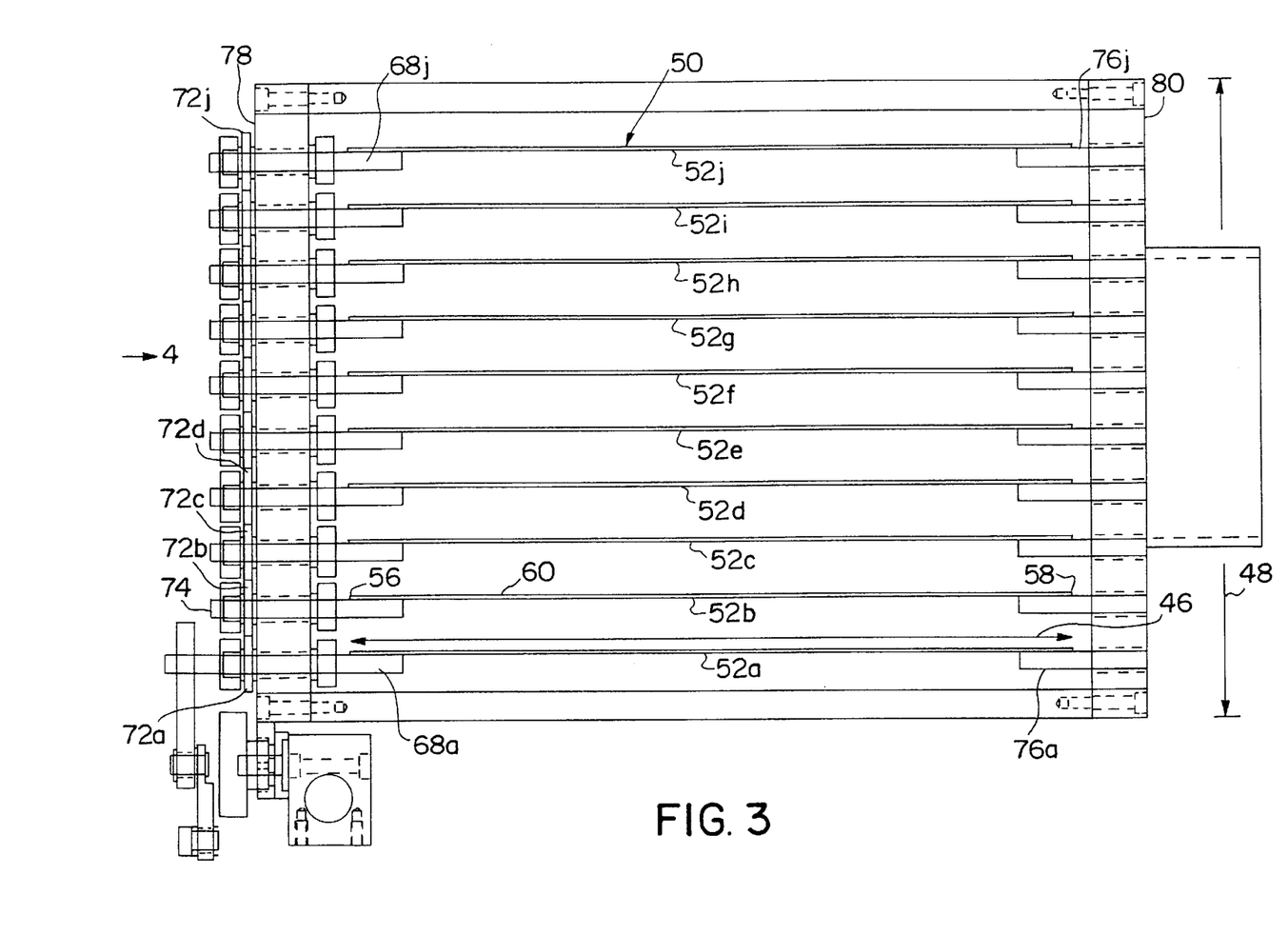
FIG. 3 is a plan view of the shutter arrangement, observed along the lines 3—3 of FIG. 2.

Although a number of processes and associated operations can be performed during the course of travel of a particular work piece through the full circular motion of the dial, of particular concern with the present invention, is a high intensity UV curing station 28 which can be part of work station 22 and which is maintained through support structures 30, 32, 34, 36 in fixed relation to the rotating dial. A source 38 of UV light is situated above the dial 14, and an associated reflector 40 directs a "blanket" of UV light which passes through shutter assembly 42, through an aperture 44, and onto the work piece 18. As an example for the curing of inks that are used for screen printing graphics on to a five inch diameter compact disc, the aperture 44 would typically be about three to four inches in diameter, and the shutter length dimension 46 as shown in FIGS. 2 and 3, would be about six inches. As shown in FIG. 3, the shutter assembly extends in the width dimension 48 for approximately four to six inches. In general, it may be understood that the curing area of interest, is approximately six inches square, as projected on the pallet 20. In FIGS. 2 and 3, it may be seen that the preferred shutter configuration 50 consists of ten shutter segments 52a–j, each of which is shown in a vertical orientation, corresponding to the full open condition of the shutter assembly.

Figure 4:
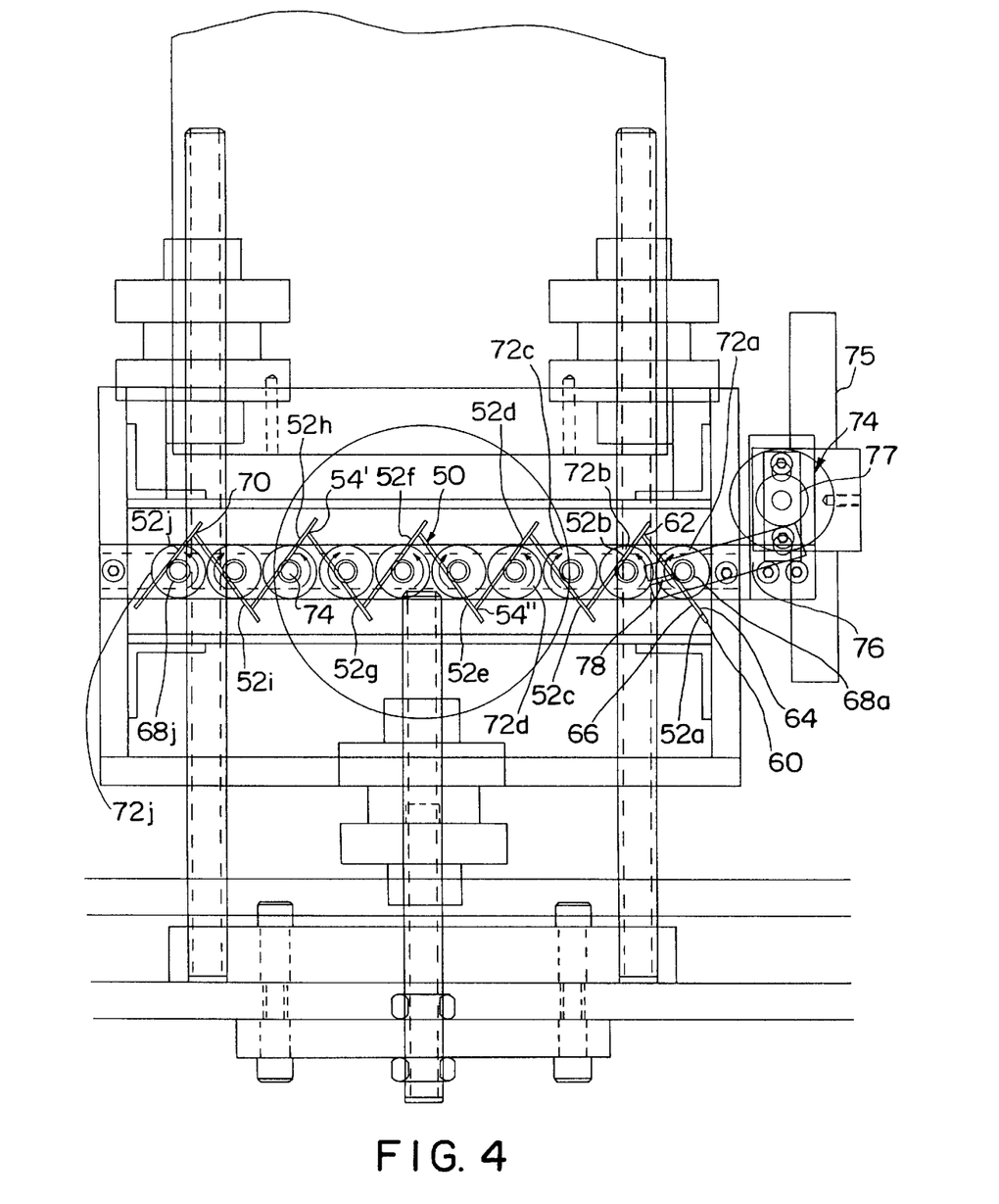

FIG. 4 shows the shutter configuration 50 in the closed condition, whereby each segment 52 has been rotated approximately 45° relative to the vertical. A first set of shutter segments 52a,c,e,g,i, thus rotates from vertical (open), counterclockwise to approximately 45°, to a closed position, whereas the other set, of alternating segments 52b,d,f,h,j, rotates from vertical, clockwise approximately 45° to the closed position. As seen in FIG. 4, when the shutter assembly is in the closed configuration, the segments as seen from an end view, define a series of "V" forms, the apexes 54 of which alternate in pointing either upwardly 54' or downwardly 54".

From FIGS. 2, 3 and 4, it is evident that each of the plurality of shutter segments 52 can be described as having longitudinally opposed ends 56,58, front and back edges 60,62, and top and bottom solid surfaces 64,66. Each segment is adjacent at least one other segment, arranged with the front 60 and back 62 edges of each segment in parallel along a first direction, and one of the front or back edge of each segment overlapping one of the top 64 or bottom 66 surfaces of an adjacent segment.

A drive hub 68a–j is rigidly connected to each segment, respectively. In the embodiment shown in FIG. 4, each hub 68 is substantially cylindrical, and the respective shutter segment is connected as a tangent to the hub. In this manner, the extent of overlap, such as at 70, can be established for convenience, rather than requiring that the edges of adjacent segments mate exactly when in the closed configuration. Each drive hub 68a–j is rigidly connected to a respective pinion gear 72a–j, each of which is the same size, and the centers 74 of which are concentric with, and on the same plane as the centers of the hubs 68. Each pinion gear e.g., 72c, engages two adjacent pinion gears e.g., 72b and 72d (except for the end gears 72a and 72j, which engage only one adjacent pinion gear 72b and 72i). In this configuration, the clockwise rotation of a given pinion gear such as 72c produces counter-clockwise rotation of the two adjacent engaged pinion gears 72b and 72d, and vice versa.

Preferably, a pneumatically actuated crank drive linkage 74 converts reciprocal linear motion of a pneumatic piston 75, into reciprocal angular motion of the drive hubs 68, via link 76. A slide bar 77 is pivotally connected to one end of link 76, with the other end of the link fixedly connected at 78 to a drive hub 68a on one of the end shutters. A stroke of the piston 75 produces an angular movement of approximately 45 degrees in each drive hub 68. Because the pinion gears are all engaged to each other, the actuation of the leading drive hub 68a and associated pinion gear 72a as described above, produces synchronous and direct rotation of the other drive hubs for actuating the associated other shutter segments through a similar cycle of opening and closing during a single full extension and retraction of the piston 75.

The respective shutter segments may also have undriven hubs 76a–j at the ends thereof opposite to the drive hubs 68a–j. The shutter assembly includes end supports 78,80 for the hubs, or similar fixturing by which extensions of the shutters are supported, with the shutter segments per se interposed between the source of UV light and the location at which the work piece having the material to be cured, will be indexed into position.

It can be appreciated that with the arrangement shown in FIGS. 2–4, the drive train, comprising the pinion gears 72, drive gear 74, and connecting link 76, with associated supports 78,80, simultaneously reciprocates the hubs and connected shutter segments rotatively through an included angle of less than 90° around respective axes of rotation which are parallel and co-planar. In particular, in the shown arrangement, when the shutter segments are closed, each segment forms an acute angle at each apex 54',54" relative to an adjacent segment. The included angle of reciprocal rotation is preferably about 45° for each segment.

Figure 5:
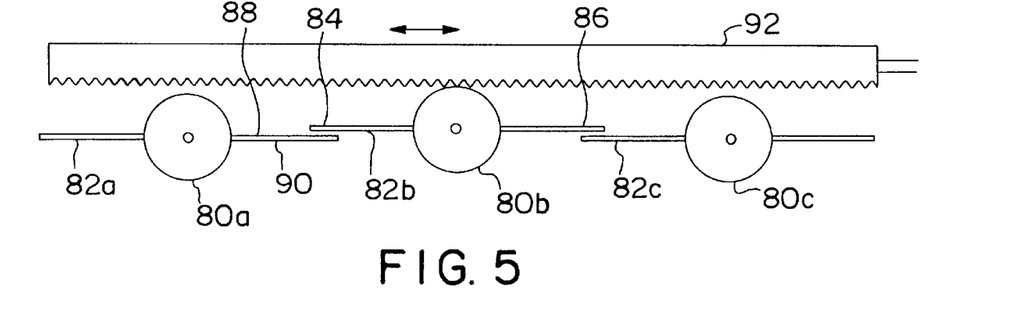
FIG. 5 is a schematic representation of a drive train according to one embodiment for implementing the multiple shutter aspect of the present invention.

FIG. 5 shows an alternative, simplified arrangement, in which a plurality of at least three drive hubs or gears 80a,b,c, each of which supports a shutter segment 82a,b,c which each have front and back edges 84,86. Each shutter segment, is adjacent at least one other segment, with one of the front or back edge of each segment overlapping one of the top or bottom surfaces 88,90 of an adjacent segment. In this embodiment, all the segments are substantially co-planar, i.e., they are substantially horizontal in overlapping relation when the shutter assembly is closed. As with the previously described embodiment, means are provided for simultaneously reciprocating each of the shutter segments through an included angle of no greater than about 90°. The means shown in FIG. 5, include a toothed drive rack 92 which can engage the toothed hubs or gears 80 and, as the drive rack reciprocates horizontally, the drive gears and thus the shutter segments, are rotated 90° clockwise to open, and 90° counterclockwise to close.

Figure 6:
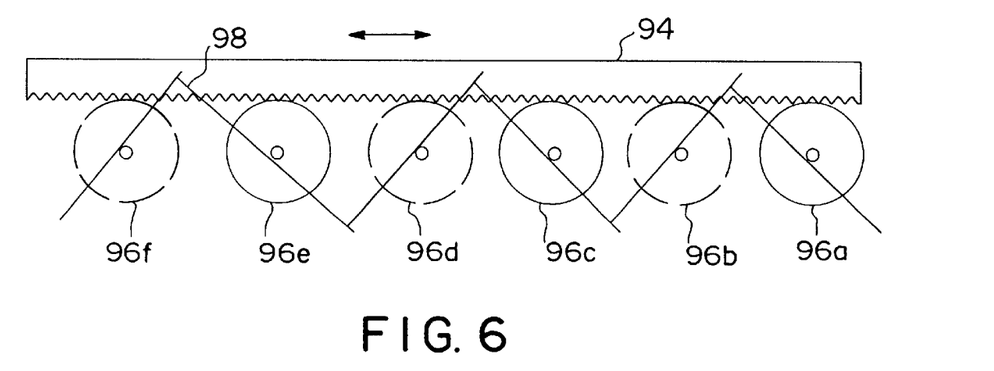
FIG. 6 is a schematic of a second embodiment for implementing the drive train of the present invention.

In the embodiment shown in FIG. 6, an arrangement is shown wherein two laterally spaced drive racks are provided (only one of which 94 is shown). The shown drive rack engages alternating gears 96a,c,e shown in solid circles, whereas the second drive rack located at the other end of the shutters, engages the drive gears 96b,d,f indicated in phantom. The drive racks reciprocate horizontally, with one 94 moving to the left as the other moves to the right, thereby imparting alternating clockwise and counterclockwise motion to adjacent segments 98. As with the embodiment shown in FIG. 4, the segments are preferably overlapping at an acute angle, with the full rotation interval to open at 45°, and likewise the rotation to close at 45°.

Figure 7:
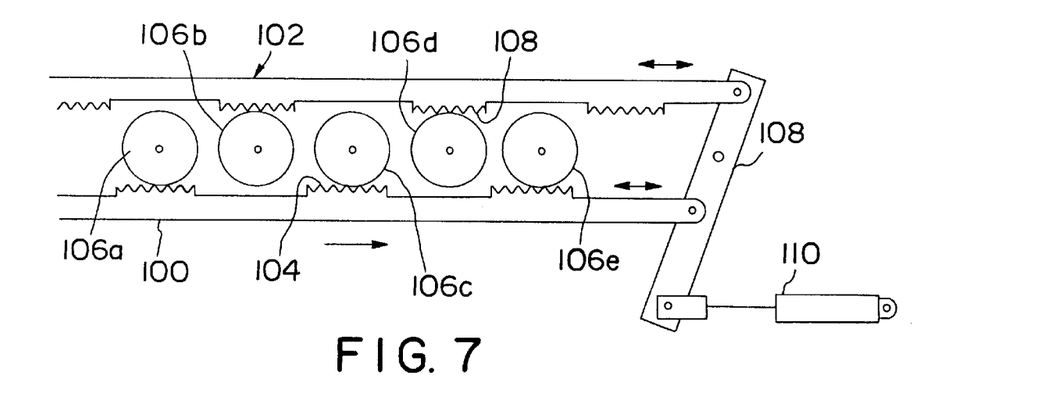
FIG. 7 is a schematic of a third embodiment for implementing the drive train of the present invention.

Yet a third drive train embodiment is shown in FIG. 7, where two drive racks 100,102 are also employed, but these can be at the same end of the shutter segments (not shown), with the lower drive rack 100 having spaced apart teeth 104 which engage alternating gears 106a,c,e, whereas the upper drive rack 102 has spaced apart teeth 108 which engage the other of the alternating gears 106b,d. The upper and lower drive racks are connected by a link member 108, which is driven by a reciprocal linear actuator 110. This link arrangement produces synchronous movement of the racks 100 and 102 in opposite directions. The link arrangement thus produces the required reciprocating rotational motion to the gears, and thus to the shutters. A shutter arrangement similar to that shown in FIGS. 4 and 6 can thus be implemented using the alternative drive mechanism of FIG. 7.

Figure 8:
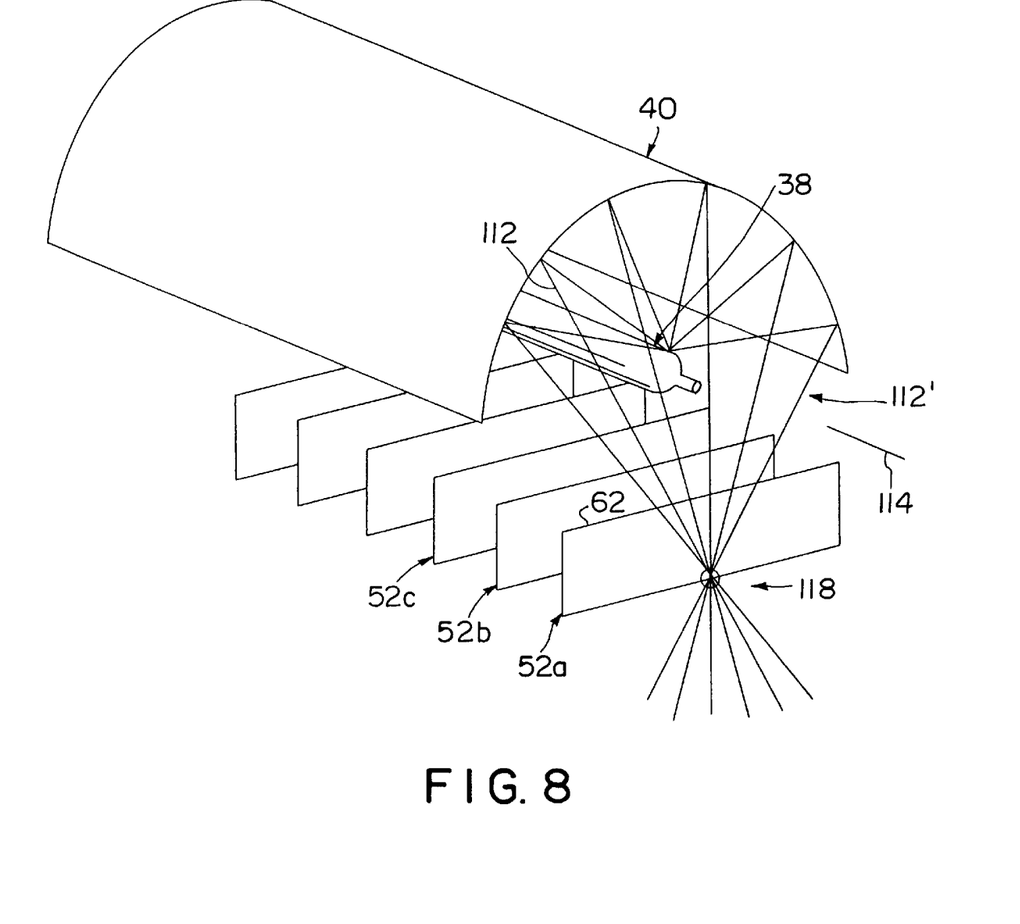
FIG. 8 is a schematic representation of the preferred arrangement of UV source tube, reflector, and shutter segment orientation.

The preferred spatial relationship of the reflector 40 and UV source tube 38 relative to the shutters, is shown in FIG. 8. The arrangement of the reflector 40 and associated UV source tube 38 in relation to the orientation of the shutter segments such as 52a, 52b and 52c, produces a UV "blanket" that is minimally interrupted by the shutters. The UV blanket can be considered as constituted from an infinite number of UV "rays", two of which 112 and 112' are shown in FIGS. 2 and 8. Each ray originates from the axis 114 of the tubular and thus elongated source bulb 38. Some of these rays such as 116 follow a direct path toward the shutters, whereas other rays impinge upon the reflector and are redirected downwardly, at an angle to the vertical. The parabolic reflector 40 is also elongated along the source axis 114. The reflected rays such as 112, 112' converge at a line 118 which is vertically under and extends parallel to the source axis 114 (i.e., axis 114 and line 118 extend into and out of the plane represented in FIG. 2). This convergence line 118 is preferably at an elevation that is within the shutter array.

This arrangement, whereby the source tube 38 and reflector 40 are elongated along tube axis 114, in a direction which is substantially perpendicular to the elongated dimension 46 of the shutters, minimizes the blockage of light by the shutters, when the shutters are in the open position. It can be appreciated that the only surface area of the open shutters which is exposed to the UV rays, is the top edge 62. The front and back surfaces 64,66, remain parallel to, and therefore do not block, the rays.

Thus, despite the greater number of shutter segments according to the present invention, relative to conventional techniques, and whereby at least a portion of some shutter segments remain in the blanket of UV light during the open condition of the shutter assembly, the negative effect on both light blockage and uniformity of exposure, is minimal.

What is claimed is:

1. In a system for periodically positioning curable material at a location subjected to high intensity ultraviolet (UV) curing light passing through a shutter which opens and closes to control duration of curing exposure, the improvement wherein said shutter comprises:

at least three shutter segments each having longitudinally opposed ends, front and back edges, and top and bottom solid surfaces, wherein each segment is adjacent at least one other segment, the segments are arranged with the front and back edges of each segment in parallel along a first direction, and one of the front or back edge of each segment substantially abuts an adjacent segment; and means are provided for simultaneously reciprocating each of said shutter segments through an actuation angle of no greater than about 90 degrees.

2. The system of claim 1, wherein the shutter segments when closed, are substantially coplanar, and the actuation angle is about 90 degrees.

3. The system of claim 1, wherein when the shutter segments are closed, each segment forms an acute angle relative to an adjacent segment.

4. The system of claim 1, wherein the actuation angle of rotation is about 45 degrees for each segment.

5. The system of claim 1, wherein the curing light originates from only one UV source tube and only one associated reflector, and wherein said tube and reflector are elongated in a direction substantially perpendicular to the longitudinal dimension of the shutter segments.

6. The system of claim 5, wherein said reflector is parabolic in section, whereby UV light is reflected toward the shutter assembly through a line of focus which extends in parallel with and is vertically below the tube.

7. The system of claim 6, wherein said line of focus is at an elevation between the front and back edges of the shutter segments when in the open configuration.

8. A system for exposing curable material to high intensity ultraviolet (UV) light through shutters which open and close to control the timing and duration of exposure, the improvement comprising:

at least four shutter segments each having longitudinally opposed ends, front and back edges, and top and bottom solid surfaces, wherein each segment is adjacent at least one other segment, the segments are arranged with the front and back edges of each segment in parallel along a first direction, and one of the front or back edge of each segment substantially abuts an adjacent segment;

a drive hub rigidly connected to each segment, respectively; and a drive train engaging all said drive hubs, for simultaneously actuating said hubs and connected shutter segments rotatively through actuation angles of no more than about 90 degrees to open and no more than about 90 degrees to close, around respective axes of rotation which are parallel and coplanar along said first direction.

9. The system of claim 8, wherein one of the front or back edge of each segment overlaps one of the top or bottom surfaces of an adjacent segment.

10. The system of claim 8, wherein when the shutter segments are closed, each segment forms an acute angle relative to an adjacent segment.

11. The system of claim 8, wherein the actuation angle of rotation is about 45 degrees for each segment.

12. The system of claim 8, wherein said drive train includes a plurality of pinion gears operatively connected respectively to each drive hub;

each pinion gear engaging at least one other pinion gear for mutual but opposite rotation; and drive means for angularly reciprocating at least one of the pinion gears, thereby reciprocating all the pinion gears, drive hubs, and shutter segments.

13. The system of claim 12, wherein the drive means includes a crank drive member which cycles through 180 degrees, a link member having one end pivotally connected to the drive member and another end connected to said at least one pinion gear, whereby one cycle of the drive member produces one opening and closing cycle of reciprocating angular motion of all the shutter segments.

14. The system of claim 13, wherein when the shutter segments are closed, each segment forms an acute angle relative to an adjacent segment.

15. The system of claim 14, wherein the actuation angle of rotation is about 45 degrees for each segment.

16. The system of claim 8, wherein said drive train includes a plurality of pinion gears operatively connected respectively to each drive hub;

a drive rack engaging all said pinion gears; and means for linearly reciprocating the drive rack.

17. The system of claim 8, wherein said drive train includes a plurality of pinion gears operatively connected respectively to each drive hub;

a first drive rack operatively engaging a first set of pinion gears consisting of every other one of all the pinion gears;

a second drive rack operatively engaging a second set of pinion gears consisting of all the pinion gears that are not engaged by the first drive rack; and means for linearly reciprocating the upper and lower drive racks synchronously and in opposite directions, whereby the first set of pinion gears all reciprocate clockwise then counterclockwise in unison while the second set of pinion gears all rotate counterclockwise then clockwise in unison.

18. The system of claim 8, including a UV source tube and associated reflector, and wherein said tube and said reflector are elongated in a direction substantially perpendicular to the longitudinal dimension of the shutter segments.

19. The system of claim 18, wherein said reflector is parabolic in section, whereby UV light is reflected toward the shutter assembly through a line of focus which extends in parallel with and is vertically below the tube.

20. The system of claim 19, wherein said line of focus is at an elevation between the front and back edges of the shutter segments when in the open configuration.

21. A UV curing station comprising:

an elongated UV source tube;

an elongated reflector partially surrounding one side of the source tube;

a shutter assembly situated at the other side of the source tube including a plurality of elongated shutter segments operable between an open configuration in which the segments are spaced apart laterally and oriented in parallel from each other to define open areas for the passage of UV light, and a closed configuration in which the segments substantially abut with each other to block the passage of UV light, wherein the shutter segments are elongated in a direction perpendicular to the elongation of the UV source tube and reflector.

22. The system of claim 21, wherein said reflector is parabolic in section, whereby UV light is reflected toward the shutter assembly through a line of focus which extends in parallel with and is vertically below the tube.

23. The system of claim 22, wherein said line of focus is at an elevation within the shutter segments when in the open configuration.

24. A method for operating a shutter assembly interposed between a UV curing light source and a work piece positioned by an indexing conveyor at a particular location beneath the source, comprising:

closing a configuration of at least four shutter segments by rotating the segments simultaneously toward each other such that adjacent segments overlap and block UV light at said location;

while the shutter configuration is closed, conveying a work piece to said location;

opening the shutter configuration by rotating the segments simultaneously through an actuation angle of no more than about 90 degrees, thereby exposing the work piece to light;

closing the shutter configuration by rotating the segments simultaneously toward each other through said actuation angle in reverse such that adjacent segments overlap and block the UV light at said location.

25. The method of claim 24, wherein the shutter segments overlap at an acute angle and open and close at an actuation angle of less than 90 degrees.

26. The method of claim 24, wherein at least four shutter segments are actuated simultaneously to open in about 0.1 second and to close in about 0.1 second.

\* \* \* \* \*